United States Patent

Grzeszczuk et al.

(10) Patent No.: US 6,782,287 B2
(45) Date of Patent: Aug. 24, 2004

(54) METHOD AND APPARATUS FOR TRACKING A MEDICAL INSTRUMENT BASED ON IMAGE REGISTRATION

(75) Inventors: Robert Grzeszczuk, San Francisco, CA (US); Ramin Shahidi, San Francisco, CA (US)

(73) Assignees: The Board of Trustees of the Leland Stanford Junior University, Stanford, CA (US); General Electric Company, Schenectady, NY (US)

( * ) Notice: Subject to any disclaimer, the term of this patent is extended or adjusted under 35 U.S.C. 154(b) by 0 days.

(21) Appl. No.: 09/892,402

(22) Filed: Jun. 26, 2001

(65) Prior Publication Data

US 2002/0077543 A1 Jun. 20, 2002

Related U.S. Application Data

(60) Provisional application No. 60/214,324, filed on Jun. 27, 2000.

(51) Int. Cl.[7] .............................................. A61B 6/00
(52) U.S. Cl. ........................................................ 600/424
(58) Field of Search ............................... 600/427, 424, 600/429, 411, 417, 402, 437, 117; 606/130; 378/4, 20, 62, 94

(56) References Cited

U.S. PATENT DOCUMENTS

| | | | | |
|---|---|---|---|---|
| 3,949,229 A | | 4/1976 | Albert | |
| 5,531,520 A | * | 7/1996 | Grimson et al. | 382/131 |
| 5,749,362 A | | 5/1998 | Funda et al. | |
| 5,795,294 A | * | 8/1998 | Luber et al. | 600/407 |
| 5,901,199 A | * | 5/1999 | Murphy et al. | 378/65 |
| 6,061,439 A | * | 5/2000 | Bleile et al. | 379/201.04 |
| 6,259,943 B1 | * | 7/2001 | Cosman et al. | 600/429 |
| 6,285,902 B1 | * | 9/2001 | Kienzle et al. | 600/427 |
| 6,314,310 B1 | * | 11/2001 | Ben-Haim et al. | 600/424 |
| 6,347,240 B1 | * | 2/2002 | Foley et al. | 600/426 |
| 6,351,661 B1 | * | 2/2002 | Cosman | 600/426 |
| 6,442,417 B1 | * | 8/2002 | Shahidi et al. | 600/429 |
| 6,490,475 B1 | * | 12/2002 | Seeley et al. | 600/426 |

* cited by examiner

Primary Examiner—Francis J. Jaworski
(74) Attorney, Agent, or Firm—McAndrews, Held & Malloy, Ltd.; Peter J. Vogel; Michael A. Dellapenna

(57) ABSTRACT

An apparatus, method and system for tracking a medical instrument, as it is moved in an operating space to a patient target site in the space, by constructing a composite, 3-D rendition of at least a part of the operating space based on an algorithm that registers pre-operative 3-D diagnostic scans of the operating space with real-time, stereo x-ray or radiograph images of the operating space. The invention has particular utility in tracking a flexible medical instrument and/or a medical instrument that moves inside the patient's body and is not visible to the surgeon.

12 Claims, 3 Drawing Sheets

METHOD AND APPARATUS FOR TRACKING A MEDICAL INSTRUMENT BASED ON IMAGE REGISTRATION

This application claims priority to U.S. Provisional Patent Application Serial No. 60/214,324 filed Jun. 27, 2000, which is incorporated in its entirety herein by reference.

FIELD OF THE INVENTION

The present invention relates to an apparatus, method and system for tracking a medical instrument in three-dimensional (3-D) space based on diagnostic scan data and intra-operative stereo images. The invention has particular application in tracking instruments, both flexible and rigid, as they are moved inside a patient's body. The invention also relates to a processor-readable medium embodying a program of instructions (e.g., software) which may be employed with the apparatus or system for implementing aspects of the tracking method.

REFERENCES

[1] R. Hofstetter, M. Slomczynski, M. Sati and L. -P. Nolte, "Fluoroscopy as an Imaging Means for Computer-Assisted Surgical Navigation," *Computer Aided Surgery* 4:65–76, (1999).

[2] R. Y. Tsai, "An Efficient and Accurate Camera Calibration Technique for 3D Machine Vision", Proceedings of IEEE Conference on Computer Vision and Pattern Recognition, Miami Beach, Fla., 1986, pages 364–374.

[3] M. J. Murphy, "An automatic six-degree-of-freedom image registration algorithm form image-guided frameless stereotaxic radiosurgery," in *Medical Physics* 24(6), (June 1997).

[4] J. Weese, G. P. Penny, T. M. Buzug, C. Fassnacht and C. Lorenz "2D/3D registration of pre-operative CT images and intra-operative X-ray projections for image guided surgery," in CARS97, H. U. Lemke, M. W. Vannier and K Inamura ed., pages 833–838, (1997).

[5] M. Roth, C. Brack, R. Burgkart, A. Zcopf, H. Gotte and A. Schwiekard "Multi-view contourless registration of bone structures using single calibrated X-ray fluoroscope," CARS99, pages 756–761, (1999).

BACKGROUND OF THE INVENTION

Various scanning techniques are known for imaging and mapping body structures, which provide information regarding the location of a target site in a patient's body for surgical or diagnostic procedures. One such technique employs still photography, videography, radiological x-rays, or angiography to produce a 2-D projection of a 3-D object.

Another technique involves (1) acquiring 2-D image scans of the operating space and internal anatomical structures of interest either pre- or intra-operatively; (2) reconstructing 3-D images based on the acquired 2-D scans; and (3) segmenting the 3-D images. The scans are typically computerized tomographic (CT) scans, positron emission tomography (PET) scans, or magnetic resonance image (MRI) scans.

The image scans are registered with the patient to provide a basis for localizing or tracking a medical instrument with respect to anatomical features or other elements in the images, as the instrument is moved within the operating field during surgery. Registration involves the point-for-point mapping of the image space to the patient space, allowing corresponding points to be mapped together. Corresponding points are those points that represent the same anatomical features in two spaces.

With registration established, appropriate equipment can be used to track the medical instrument relative to internal structures of the patient as it is navigated in and around the patient target site during surgery. Images of the target site are displayed to assist the user (e.g., the surgeon) in navigating to the target site. Conventional tracking equipment includes a structure to define a 3-D reference coordinate system relative to the patient or operating space.

One such structure used for instrument localization or tracking in neurosurgery is a large ring-like device which surrounds the patient's head and is fixed relative thereto. The ring establishes a 3-D coordinate system with respect to the patient's head. A separate calibration unit having an array of rod elements is fixed to the ring to surround the head during the generation of scan and/or 2-D images. The rods, which have known coordinates in the 3-D coordinate system defined by the ring, produce spots in the scans. Other features in the volume scans can then be assigned coordinates in the 3-D coordinate system by correlation with the known coordinates of the spots produced by the rod elements.

After the images are made, the calibration unit is detached from the ring, and a guidance arc calibrated to the 3-D coordinate system of the ring is attached in its place. The arc provides coordinate reference information to guide the instrument which is usually attached to the arc.

Cranial implants of radio-opaque or MRI-opaque materials have also been used as a localization structure. Three or more of such implants are made and used to establish a 3-D coordinate system.

Another type of localization device is a fiducial structure which is positioned in the operating space for calibrating the operating space in terms of a 3-D coordinate framework. The fiducial structure includes a set of fiducial points connected by a frame constructed to hold the points in fixed spatial relation to each other. The 3-D operating space framework is derived by computation from two 2-D projections of a calibration image pair obtain from video cameras made with the fiducial structure positioned in the operating space. After the calibration image pair is made the fiducial structure is removed, and a standard projection algorithm is used to reconstruct the operating space framework from the calibration image pair. Such framework is then aligned with a 3-D volume scan framework and can be used to locate and track a medical instrument in the operating space, so long as the cameras remain in fixed positions relative to the operating space.

A basic disadvantage with these conventional 3-D reference frame structures is that they add an extra degree of complication to the tracking process by establishing a coordinate framework for the operating space.

In the area of computer-assisted spine surgery various systems have been proposed for registration and localization. These systems are generally similar in the methodology used and the functionality provided, with the majority of such systems employing optical trackers for the purpose of registration and localization. Typically, the vertebrae of interest is fully exposed intra-operatively, and a small number of distinct anatomical landmarks are digitized for the purpose of coarse registration. Subsequently, a larger number of points are digitized on the surface of the vertebrae to refine the registration with a surface matching technique. The procedure is often cumbersome, time consuming, and of limited accuracy. This is mainly due to difficulties in identifying characteristic anatomical landmarks in a reproducible fashion and inherent inaccuracies of surface matching techniques. While dynamic reference frames (DRFs) are commonly used to monitor target movement, any safeguarding against DRF misregistration requires the entire process, including the laborious manual digitization part to be repeated. The problem is exacerbated in procedures involving multiple vertebrae (e.g., cage placements) requiring context of percutaneous procedures, because they rely on the target structure being directly visible to the optical tracking device.

Recently, there has been some interest in fluoroscopy as an intra-operative imaging modality [1]. The relative low cost and pervasiveness of C-Arm devices in modern operating rooms (ORs) drives this interest. Most of these attempts focus on improving conventional 2D navigation techniques via tracking of the C-Arm and re-projecting pre-operative CT data onto multiple planes. Such techniques are helpful in lowering the amount of ionizing radiation delivered to the patient and the OR staff during free-hand navigation and also in providing more information to the surgeon about the relative position of the surgical tools with respect to the patient's anatomy. However, they essentially automate and streamline the current workflow and rely on the surgeon's ability to create a complex spatial model mentally.

Thus, there is a need for a more efficient and effective technique for performing registration and localization to track a medical instrument in an operating space that eliminates the need to establish an operating space framework and the complications associated with DRFs.

SUMMARY OF THE INVENTION

It is therefore an object of this invention to provide a technique that employs stereoscopic registration in order to relate a patient's anatomy to pre-operative diagnostic scans in 3-D without the aid of an external calibration device.

It is another object of this invention to provide a technique that is able to track a surgical tool and localize it with respect to the patient's anatomy and pre-operative diagnostic scans using intra-operative fluoroscopy for in situ registration.

Advantageously, the technique of the present invention does not require a fixed fiducial registration structure, nor does it require a fixed camera position relative to the operating space. Moreover, the technique provides a way of tracking a surgical tool with respect to a 3-D model, instead of using a 2-D projection.

In one aspect, the invention provides an apparatus for use in an image-guided surgical or a diagnostic procedure for tracking an instrument in an operating space that includes a target site of a patient. The apparatus comprises a data-storage medium for storing scan data representing scans of the operating space including the patient target site; an image capture device adapted to capture at least two stereo images of the operating space including the patient target site and such instrument during the image-guided surgical or diagnostic procedure; a display device; and a processor in communication with the data-storage medium, the image capture device, and the display device. The processor is operable to register selected scan data with the stereo images without using a fiducial structure, construct a composite, three-dimensional rendition showing features from the selected scan data and the stereo images, and display the composite rendition on the display device, so as to enable a user to track the instrument as it is moved within the operating space to a selected position with respect to the patient target site.

The processor preferably constructs the composite rendition using stereo photogrammetry to extract three-dimensional information from projective images, and the image capture device preferably comprises a plurality of x-ray devices adapted to capture at least two stereo radiographic images.

The apparatus is capable of tracking an instrument, which may be flexible or rigid, not visible to a user. In particular, the apparatus may be used to track a flexible instrument such as a flexible catheter through a vascular network in a patient. In such an arrangement, the data-storage medium of the apparatus stores scan data representing scans of the vascular network, and the image capture device, in the form of an x-ray device, is adapted to capture at least two stereo radiographic images of vascular network and such instrument during the image-guide surgical or diagnostic procedure. The composite rendition is displayed on the display device, so as to enable a user to track and navigate the flexible instrument as it is moved through a selected path in the vascular network to a selected position in the patient's body.

In another aspect, the invention involves a method for use in an image-guided surgical or a diagnostic procedure for tracking an instrument, which may be flexible or rigid, in an operating space that includes a target site of a patient. The method may be used to track such an instrument whether or not it is visible to a user. The method comprises storing scan data representing scans of the operating space including the patient target site; capturing at least two stereo images of the operating space including the patient target site and such instrument during the image-guided surgical or diagnostic procedure; registering selected scan data with the stereo images without using a fiducial structure; constructing a composite, three-dimensional rendition showing features from the selected scan data and the stereo images; and displaying the composite rendition, so as to enable a user to track the instrument as it is moved within the operating space to a selected position with respect to the patient target site.

Preferably, the constructing comprises constructing the composite rendition using stereo photogrammetry to extract three-dimensional information from projective images, and the capturing comprises capturing at least two radiographic images of the operating space including the patient target site and such instrument during the surgical or diagnostic procedure.

Another aspect of the invention provides a processor-readable medium embodying a program of instructions for execution by a processor for performing a method, used in an image-guided surgical or a diagnostic procedure, for tracking an instrument in an operating space that includes a target site of a patient. The program of instructions comprises instructions for performing the above-described method.

DETAILED DISCRIPTION OF THE INVENTION

The general set-up of fluoroscopic imaging for computer-assisted surgery is described in document [1] listed in the "References" section of this application. The contents of that document are incorporated by reference herein.

I. System Overview

Figure 1:
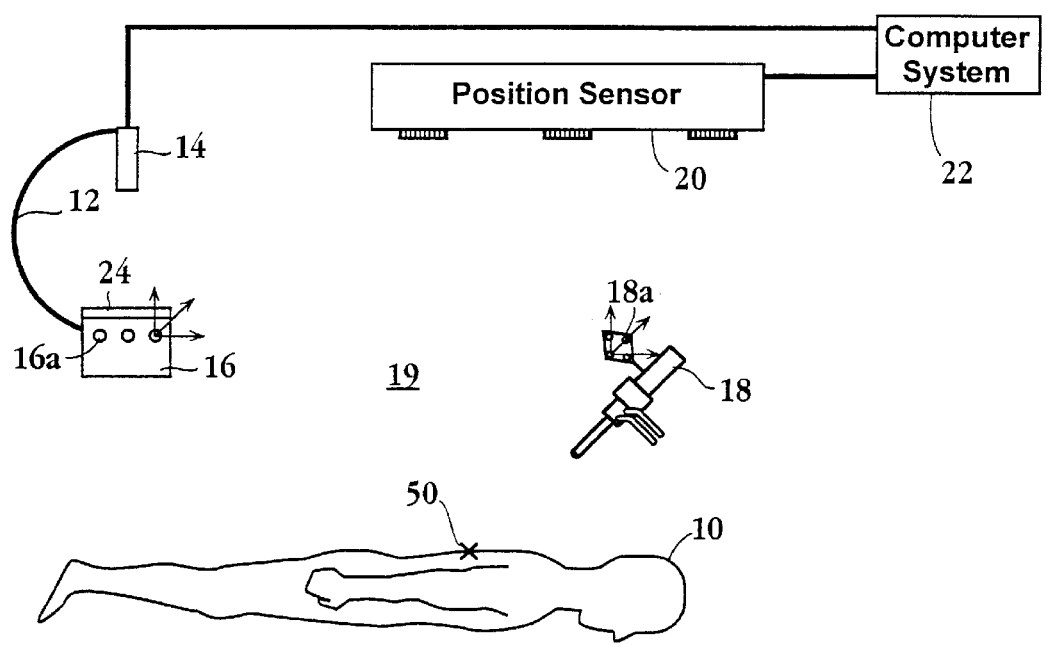
FIG. 1 is a partially perspective, partially schematic view of an image-guided surgery system, according to embodiments of the invention.

Referring to FIG. 1 a mobile fluoroscopic device 12 is used for intra-operative, free-hand imaging of selected portions of the anatomy of a patient 10. Fluoroscopic device 12 is preferably a C-Arm of the type which may be obtained from General Electric, Milwaukee, Wis. The mobile fluoroscopic device includes an X-ray camera 14 and an image intensifier 16. The system also includes a surgical instrument 18, which may be any of a variety of devices including a catheter having a flexible or rigid construction. Each of the C-arm/image intensifier and surgical instrument is equipped with emitters 16a and 18a respectively that define local coordinate systems for each of those components. The emitters may be infrared light-emitting diode (LED) markers which are in communication with a tracking device or position sensor 20 which may be an optical/electronic device, such as an Optotrack available from Northern Digital, Waterloo, Ontario, Canada. The position sensor tracks these components within an operating space 19, and supplies data needed to perform coordinate transformations between the various local coordinate systems to a computer system 22, such as a workstation computer of the type available from Sun Microsystems, Mountain View, Calif. or Silicon Graphics Inc., Mountain View, Calif. The NTSC video output of camera 14 is also processed by the computer system. A video framegrabber board, such as an SLIC-Video available from Osprey Systems, Cary, N.C., may also be employed to allow loading of gray-scale images from the video buffer of the C-arm to the computer system.

Figure 2:
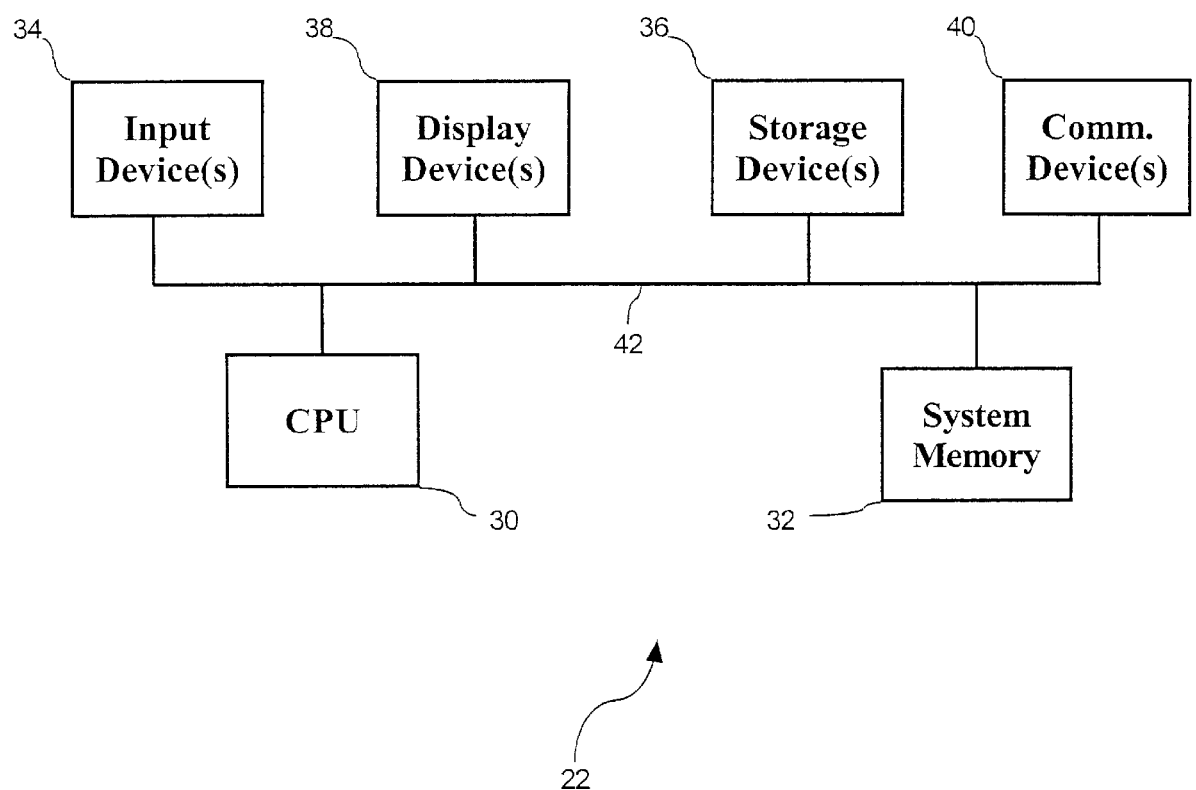
FIG. 2 is a schematic diagram depicting the architecture of a computer system which may be used in the image-guided surgery system.

The general architecture of such a computer system is shown in more detail in FIG. 2. The computer system includes a central processing unit (CPU) 30 that provides computing resources and controls the computer. CPU 30 may be implemented with a microprocessor or the like, and may also include a graphics processor and/or a floating point coprocessor for mathematical computations. Computer 22 also includes system memory 32 which may be in the form of random-access memory (RAM) and random-access memory (ROM). Input device(s) 34, such as a keyboard, mouse, foot pedal, stylus, etc., are used to input data into the computer. Storage device(s) 36 include a storage medium such as magnetic tape or disk, or optical disk, e.g., a compact disk, that are used to record programs of instructions for operating systems, utilities and applications. The storage device(s) may be internal, such as a hard disk and may also include a disk drive for reading data and software embodied on external storage mediums such as compact disks, etc. Storage device 36 may be used to store one or more programs and data that implement various aspects of the present invention, including the registration and tracking procedures. One or more display devices 38 are used to display various images to the surgeon during the surgical procedure. Display device(s) 38 are preferably high-resolution device(s). The computer may also include communications device(s) 40, such as a modem or other network device for making connection to a network, such as a local area network (LAN), Internet, etc. With such an arrangement, program(s) and/or data that implement various aspects of the present invention may be transmitted to computer 22 from a remote location (e.g., a server or another workstation) over a network. All major system components of the computer may connect to a bus 42 which may be more than one physical bus. Bus 42 is preferably a high-bandwidth bus to improve speed of image display during the procedure.

Figure 3:
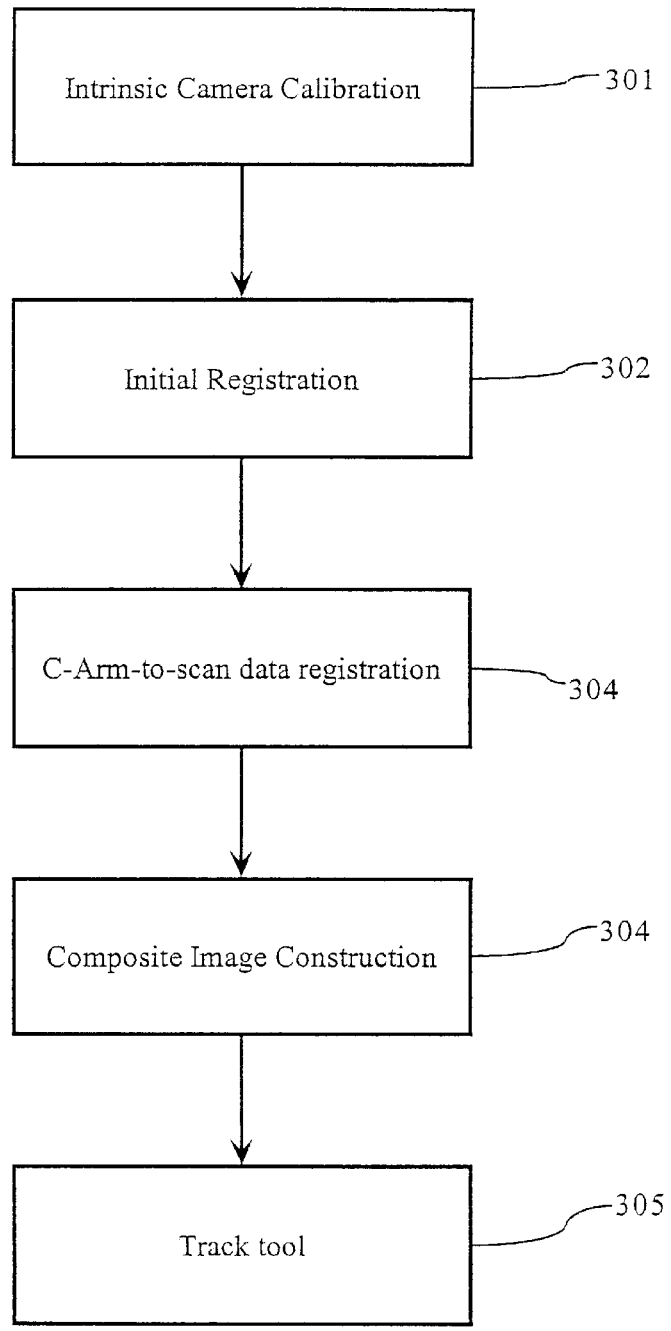
FIG. 3 is a flow chart illustrating an image-guided surgical method, according to embodiments of the invention.

Referring to the flow chart of FIG. 3, an overview of the general steps of an image-guided surgical method according to embodiments of the present invention is illustrated. Initially, in step 301, intrinsic camera calibration is performed. In step 302, image data acquired by camera 14 is used to register a pre-operative CT data set (e.g., 130 slices, 512×512, 1.0 mm thick) to the patient's reference frame.

During the course of the registration procedure, the system operator performs an initial registration of the patient's anatomy to the pre-operative CT data set by taking at least two protocoled fluoroscopic views (e.g., an AP view and a lateral view) of the operating space 19, including a patient target site 50 (e.g., a target vertebrae). These images are then used to compute the C-Arm-to-CT data set registration in step 303 using a fully automatic technique described in detail below. As a result, the position and orientation of the C-Arm's camera is obtained in the reference frame of the CT data set.

This information is then used, together with the position and orientation of the camera in the reference frame of the tracking device to follow the future relative motions of the camera. Tracking data is used to monitor the relative position changes of camera 14 with respect to the patient during free-hand navigation.

Misregistration, due to either patient movement or system error, can be detected at any time by comparing the predicted Digitally Reconstructed Radiograph (DRR) to the actual fluoroscopic image, at which time the objects can be re-registered within seconds.

With surgical tool being visible in at least two fluoroscopic views, the tool is then back-projected into the reference frame of the CT data set using standard stereoscopic techniques that are well known in the computer vision community (step 304). The position and orientation of the tool can then be visualized with respect to a 3-D model of the anatomical structure of interest. Using this composite rendition, in which the tool is present in the reference frame of the scan data, the tool is tracked (step 305). The tool can also be tracked externally (e.g., using the tracking device already employed, or a robotic interface) to facilitate a variety of surgical procedure types.

II. Intrinsic Camera Calibration

Before use, the system is calibrated to eliminate imaging distortions and extract parameters required to characterize the imaging system. During the process of intrinsic camera calibration, a set of parameters that characterize the internal geometry of the imaging system is obtained. All of these parameters are well documented in the computer vision literature [2]. They include effective focal length (i.e., the exact distance from the X-ray source to the image plane), focal spot (i.e., the exact place where the optical axis pierces the image plane), magnification factors, and pincushion distortions. It is also well understood that many of the C-Arm's intrinsic parameters vary with orientation. For example, the focal length and focal spot will be different for vertical and horizontal positioning, due to mechanical sag of the arm. Similarly, the pincushion distortion depends on the orientation of the device with respect to the Earth's magnetic field, and external source electromagnetic fields.

For these reasons, a calibration jig 24 is placed in the field-of-view of the of the X-ray camera, e.g., fixed to the face of the image intensifier, in order to adaptively calibrate the system every time an image is acquired. The intrinsic parameters thus generated are used during the registration phase. It should be noted that the calibration jig 24 is used exclusively for the purpose of correcting distortion of the imaging system and not for the purpose of registration.

III. Extrinsic Camera Calibration and Registration

Once the intrinsic camera parameters are measured, the imaging system can be registered to the patient. Given a CT study of the relevant anatomy in the operating space and a fluoroscopic image of the same anatomy, the task involves finding the position and orientation of camera 14 in the reference frame of the CT study that produced the image. For this purpose, a technique used by a commercial frameless image-guided radiosurgery system (Cyberknife, Accuray Inc., Sunnyvale, Calif., USA) [3] is employed. In this approach, the system hypothesizes about the camera's actual six degrees of freedom (DOF) position by introducing a virtual camera and computing a simulated radiograph (e.g., DRR). The radiograph represents the actual patient position. If the DRR matches the radiograph exactly, the virtual camera position identifies the actual camera position and thus the registration is found; otherwise another hypothesis is formed. In practice, the accuracy of such basic radiograph-to-DRR registration method can be substantially improved if two or more views of the same anatomy can be used. In this scenario, it is assumed that the relative positions of the cameras are known (e.g., from tracking device 20). Therefore, instead of finding two or more independent camera positions [4], the task can be reformulated as finding the pose of CT study with respect to the rigid configuration of multiple cameras. In essence, the registration process can be viewed as an extrinsic calibration of an abstract imaging system consisting of multiple, rigidly mounted cameras.

The radiograph-to-DRR registration procedure has three parts: (1) exploring the range of possible patient positions to be represented in the DRRs (i.e., hypothesis formation strategy), (2) identifying those elements in the images (image features) that most effectively capture information about the patient pose, and then (3) using a comparison statistic or cost function for the two sets of image feature data to indicate when the best match has been achieved.

There are three fundamental ways of generating hypotheses for possible patient placement. One approach, called matched filter area correlation, generates a single reference image from a DRR representing the desired patient position from the camera point of view. This reference image, or part thereof, is shifted and rotated relative to the acquired image until the best fit is achieved, in a manner of a sliding window matched filter. A second approach, referred to herein as interpolative area correlation, consists of calculating a set of reference DRRs that samples a full range of possible patient positions and orientations, and then making an interpolative comparison of the acquired fluoroscopic image with each of the DRRs. Using two cameras, either of the aforementioned methods can accurately measure all three translational and one rotational degree of freedom, provided there is no out-of-plane degrees of freedom [6]. A third method consists of interactively re-projecting DRRs while perturbing the pose of the patient image in the CT study, until a DRR is made that matches the fluoroscopic image. The iterative re-projection technique can accurately measure all six DOFs and is the approach taken in the present invention.

Comparison of the DRRs and acquired radiographs is a problem in pattern recognition. The sets of image data used to compare two images are called feature vectors. The most primitive feature vector is simply the complete set of pixel gray-scale values, where each pixel's brightness is the magnitude of a vector component. More sophisticated feature vectors are usually sought to emphasize the important large-scale structure in the image and minimize the extraneous information and noise. Formal systems of feature extraction involve recasting the original gray-scale feature vector on an orthogonal system of eigenvectors that relate to large-scale patterns that are not necessarily physical structures. Heuristic feature vectors identify the positions and shapes of physical edges, boundaries, and other discernible structures.

The DRR and radiograph feature vectors A and B are compared using a similarity statistic or cost function. This can be simply the cross-correlation coefficient $r = A \cdot B = \cos\theta$, where A and B have been normalized to unit length. (The vectors can be centered on their means before normalization, which gives Pearson's correlation coefficient.) A more general and flexible comparison can be made with the chi-squared statistic: $\chi^2 = \Sigma(A_i - Bi)^2/w_i^2$, where each vector component is weighted according to both its reliability and usefulness, and the vectors are not necessarily normalized. When the vectors are normalized, and all vector components carry equal weight, $\chi^2$ is proportional to 1-r.

IV. Image Processing

For fiducial-based registration, the fluoroscope image contrast is expanded and then thresholded to highlight the fiducial shadows. The image-plane coordinates of the fiducials are automatically extracted using one of three methods: (1) A Sobel edge filter is convolved across the image to further enhance the fiducials, the image is thresholded again, and then x and y moments are computed in the neighborhood of the bright fiducial edge features; (2) a matched filter representing the shadow of the fiducial is convolved across the image and the convolution maxima are isolated by thresholding; (3) if spherical fiducials have been used, a circular Hough transform is applied to the image, resulting in a bright maximum at the center of each fiducial shadow. Registration of skeletal landmarks is accomplished by edge-filtering the fluoroscope and DRR reference images and then locating the points where the anatomical edges intersect line segments at fixed positions in the images. These points make up the feature vectors for the radiographs and DRRs. With eight to ten feature points in each fluoroscope view, the translational and rotational registration can again achieve ±0.2 mm and ±0.5 degrees precision, respectively.

If the fluoroscope images have a pixel pitch of 1.0 mm, the position of a 2–3 mm diameter spherical fiducial can be found with a precision of ±0.2 mm. This yields a translational registration precision of 0.2 mm or better. The rotational precision depends on the fiducial spacing and the angle of projection of the fiducial configuration in the fluoroscope image. For fiducials spaced 25 mm apart a typical projection angle will resolve out-of-plane rotations with a precision of ±0.5 degrees.

V. Features and Advantages

Various factors differentiating the technique and solution of the present invention from that of others include: selecting fluoroscopy for the in situ imaging technique, using stereo photogrammetry to extract 3-D information from projective images, as well as using a robust, precise and practical registration method.

Unlike all currently available 3-D spinal navigation packages, which require full exposure of the vertebral body for the sake of registration and real-time optical tracking, the technique of the present invention employs fluoroscopic imaging and registration using percutaneously implanted markers or skeletal anatomy as a minimally invasive approach. This helps in the guiding of surgical tools using pre-operative 3-D diagnostic scans. While the technique of the present invention does not use a real-time DRF for the sake of target movement monitoring, periodic re-registration is much more practical than in conventional approaches: misregistration can be detected and eliminated by simply re-acquiring two new fluoroscopic images and running a fairly automatic procedure that requires little or no intervention by the operator. The registration technique has been adopted from Cyberknife's radiation treatment methodology, which has been shown to register either fiducial markers or skeletal anatomy with sub-millimeter and sub-degree precision in all six degrees of freedom and computation efficiency leading to a time scale of approximately one second to complete the entire registration process. Additional digital re-projection techniques using off-the-shelf computer graphics hardware will further enhance the robustness, accuracy, and performance of the registration method.

Similarly, the registration method of the present invention coupled with more sophisticated visualization and biomechanical modeling techniques can potentially be generalized to handle non-rigid deformations resulting from intervertebral displacement. This would allow the techniques of the present invention to be applied in clinical scenarios that involve more than a single vertebral body, without cumbersome patient fixation or making assumptions about unchanged pose between the time of the scan and intra-operative positioning. The ability to intra-operatively register articulated, deformable spinal anatomy in near real-time and with high accuracy would be a critical improvement over existing systems.

An important differentiating factor of the present invention is that it provides the ability to track surgical tools with respect to the patient's anatomy as defined by a pre-operative diagnostic scan. Unlike traditional approaches where optical tracking is used to follow the surgical tools, the techniques of the present invention employ fluoroscopy for both registration and tool tracking with respect to a 3-D model from the diagnostic scan. This permits the system of the present invention to be applied in the context of minimally invasive percutaneous procedures where the tool may not be exposed and visible to the tracking device. This is particularly advantageous for flexible and/or articulated effectors, which cannot be tracked optically.

Another benefit of the present invention's approach is more effective use of the fluoroscope with less exposure to ionizing radiation on the part of the patient as well as the surgeon, because instrumented fluoroscopy can be used in a more controlled manner than during conventional free-hand imaging.

Finally, the present invention does not use a fixed fiducial registration structure, nor require a fixed camera position.

VI. System Implementation

As previously noted, various aspects of the present invention, such as registering the operating space to the pre-operative data set, registering the C-Arm to the pre-operative data set to place the C-Arm's camera in the reference frame of the pre-operative data set, and constructing and displaying images/3-D composite renditions to track the tool as it is moved in the operating space may be implemented by a program of instructions (i.e., software). Software implementing one or more of these aspects may be written to run with existing software used for computer-assisted/image-guided surgery.

The software for any or all of these tasks may be fetched by the processor from RAM in computer system 22 for execution. The software may be stored in a storage medium in storage device 36 and transferred to RAM when in use. Alternatively, the software may be transferred to RAM through communications device 40. More broadly, the software may be conveyed by any medium that is readable by the CPU. Such media may include, in addition to various magnetic and optical media, various communication paths throughout the electromagnetic spectrum including infrared signals, signals transmitted through a network or the Internet, and carrier waves encoded to transmit the software.

As an alternative to software implementation, the above-described aspects of the invention also may be implemented with functionally equivalent hardware using discrete components, application specific integrated circuits (ASICs), digital signal processing circuits, or the like. Such hardware may be physically integrated with the computer processor(s) or may be a separate device which may be embodied on a computer card that can be inserted into an available card slot in the computer.

Thus, the above-described aspects of the invention can be implemented using software, functionally equivalent hardware, or combination thereof. The diagrams and accompanying description provide the functional information one skilled in the art would require to implement a system to perform the functions required using any of these programming tools.

As should be readily apparent from the foregoing description, the present invention provides a method, apparatus and system for tracking a surgical tool, flexible or rigid, and localizing it with respect to the patient's anatomy and pre-operative 3-D diagnostic scans using intra-operative fluoroscopy for in situ registration, without external calibration devices or fixing camera position. The resulting system leverages equipment already commonly available in operating rooms while providing a new, cost-effective medical instrument tracking technique that is free of many current limitations in the field. The computer-assisted tracking system of the present invention, which provides 3-D navigation and guidance for a surgeon, offers many advantages. It improves the accuracy, reduces risk, minimizes the invasiveness, and shortens the time it takes to perform a variety of neurosurgical and orthopedic procedures, particularly of the spine.

While embodiments of the invention have been described, it will be apparent to those skilled in the art in light of the foregoing description that many further alternatives, modifications and variations are possible. The invention described herein is intended to embrace all such alternatives, modifications and variations as may fall within the spirit and scope of the appended claims.

What is claimed:

1. An apparatus for use in an image-guided surgical or a diagnostic procedure for tracking an instrument in an operating space that includes a target site of a patient, the apparatus comprising:
    (a) a data-storage medium for storing scan data representing scans of the operating space including the patient target site;
    (b) an image capture device adapted to capture at least two radiographic stereo images of the operating space including the patient target site and such instrument during the image-guided surgical or diagnostic procedure;
    (c) a display device; and
    (d) a processor in communication with the data-storage medium, the image capture device, and the display device for:
        (i) registering selected scan data with the stereo images without using a fiducial structure,
        (ii) constructing a composite, three-dimensional rendition showing features from the selected scan data and the stereo images, and
        (iii) displaying the composite rendition on the display device, so as to enable a user to track the instrument as it is moved within the operating space to a selected position with respect to the patient target site.

2. The apparatus of claim 1, wherein the processor constructs the composite rendition using stereo photogrammetry to extract three-dimensional information from projective images.

3. The apparatus of claim 1, wherein the image capture device comprises a x-ray device.

4. The apparatus of claim 1, wherein the apparatus is capable of tracking an instrument not visible to a user.

5. The apparatus of claim 1, wherein the apparatus is capable of tracking a flexible instrument not visible to a user.

6. An apparatus for use in an image-guided surgical or a diagnostic procedure for tracking a flexible instrument such as a flexible catheter through a vascular network in a patient, the apparatus comprising:

(a) a data-storage medium for storing scan data representing scans of the vascular network;

(b) an x-ray device adapted to capture at least two stereo radiographic images of vascular network and such instrument during the image-guided surgical or diagnostic procedure;

(c) a display device; and (d) a processor in communication with the data-storage medium, the x-ray device, and the display device for:
  (i) registering selected scan data with the stereo images without using a fiducial structure,
  (ii) constructing a three-dimensional, composite rendition showing features from the selected scan data and the stereo images, and
  (iii) displaying the composite rendition on the display device, so as to enable a user to track and navigate the flexible instrument as it is moved through a selected path in the vascular network to a selected position in the patient's body.

7. A method for use in an image-guided surgical or a diagnostic procedure for tracking an instrument in an operating space that includes a target site of a patient, the method comprising:

(a) storing scan data representing scans of the operating space including the patient target site;

(b) capturing at least two radiographic stereo images of the operating space including the patient target site and such instrument during the image-guided surgical or diagnostic procedure;

(c) registering selected scan data with the stereo images without using a fiducial structure;

(d) constructing a composite, three-dimensional rendition showing features from the selected scan data and the stereo images; and (e) displaying the composite rendition, so as to enable a user to track the instrument as it is moved within the operating space to a selected position with respect to the patient target site.

8. The method of claim 7, wherein the constructing (d) comprises constructing the composite rendition using stereo photogrammetry to extract three-dimensional information from projective images.

9. The method of claim 7, wherein the tracked instrument is not visible to a user.

10. The method of claim 7, wherein the tracked instrument is a flexible instrument not visible to a user.

11. A processor-readable medium embodying a program of instructions for execution by a processor for performing a method, used in an image-guided surgical or a diagnostic procedure, for tracking an instrument in an operating space that includes a target site of a patient, the program of instructions comprising:

(a) instructions for storing scan data representing scans of the operating space including the patient target site;

(b) instructions for capturing at least two radiographic stereo images of the operating space including the patient target site and such instrument during the image-guided surgical or diagnostic procedure;

(c) instructions for registering selected scan data with the stereo images without using a fiducial structure;

(d) instructions for constructing a composite, three-dimensional rendition showing features from the selected scan data and the stereo images; and (e) instructions for displaying the composite rendition, so as to enable a user to track the instrument as it is moved within the operating space to a selected position with respect to the patient target site.

12. The processor-readable medium of claim 11, wherein the constructing instructions (d) comprises instructions for constructing the composite rendition using stereo photogrammetry to extract three-dimensional information from projective images.

* * * * *